(12) United States Patent
Cao

(10) Patent No.: US 10,706,015 B2
(45) Date of Patent: Jul. 7, 2020

(54) SYSTEM AND METHOD FOR MANAGING A WORKFLOW FOR BIOMEDICAL DEVELOPMENT

(71) Applicant: LifeScienceIT LLC, Novato, CA (US)

(72) Inventor: Yuehua Cao, Novato, CA (US)

(73) Assignee: Yuehua Cao, Novato, CA (US)

( * ) Notice: Subject to any disclaimer, the term of this patent is extended or adjusted under 35 U.S.C. 154(b) by 281 days.

(21) Appl. No.: 15/947,719

(22) Filed: Apr. 6, 2018

(65) Prior Publication Data

US 2019/0311048 A1    Oct. 10, 2019

(51) Int. Cl.

| | | |
|---|---|---|
| G06F 16/17 | (2019.01) | |
| G16H 10/20 | (2018.01) | |
| G06F 16/11 | (2019.01) | |
| G06F 16/18 | (2019.01) | |
| G16B 40/00 | (2019.01) | |
| G16B 50/00 | (2019.01) | |

(52) U.S. Cl.
CPC ........ G06F 16/1734 (2019.01); G06F 16/128 (2019.01); G06F 16/1805 (2019.01); G16B 40/00 (2019.02); G16B 50/00 (2019.02); G16H 10/20 (2018.01)

(58) Field of Classification Search
CPC .... G06F 16/1734; G06F 19/324; G06Q 10/10
See application file for complete search history.

(56) References Cited

U.S. PATENT DOCUMENTS 6,236,994 B1    5/2001  Swartz et al.
7,970,630 B2 *  6/2011  Fagan ................... G06F 19/324
                                                        705/2

FOREIGN PATENT DOCUMENTS

WO    2014/033747 A2    3/2014

OTHER PUBLICATIONS

International Search Report (ISR) and Written Opinion (WO) of the International Searching Authority of PCT/US2019/023459 dated Jun. 21, 2019, 12 pages.
Notification of Receipt of Search Copy from the International Preliminary Examining Authority for PCT/US2019/023459, dated May 3, 2019, 1 page.

* cited by examiner

*Primary Examiner* — Etienne P Leroux

(57) ABSTRACT

A method and system for managing a workflow for producing a biostatistical analysis (BA) of biomedical data. The data originates from a milestone (or snapshot) of a clinical study performed by, or on behalf of a life science company that performs the BA. The data may be from a blinded or un-blinded clinical study. SAS programs are used for the BA. An audit trail is produced to track changes to any of the data or programs used during the course of the workflow. The programs and data used to produce reported results from the BA are stored in electronic format for sending to a regulatory agency.

19 Claims, 10 Drawing Sheets

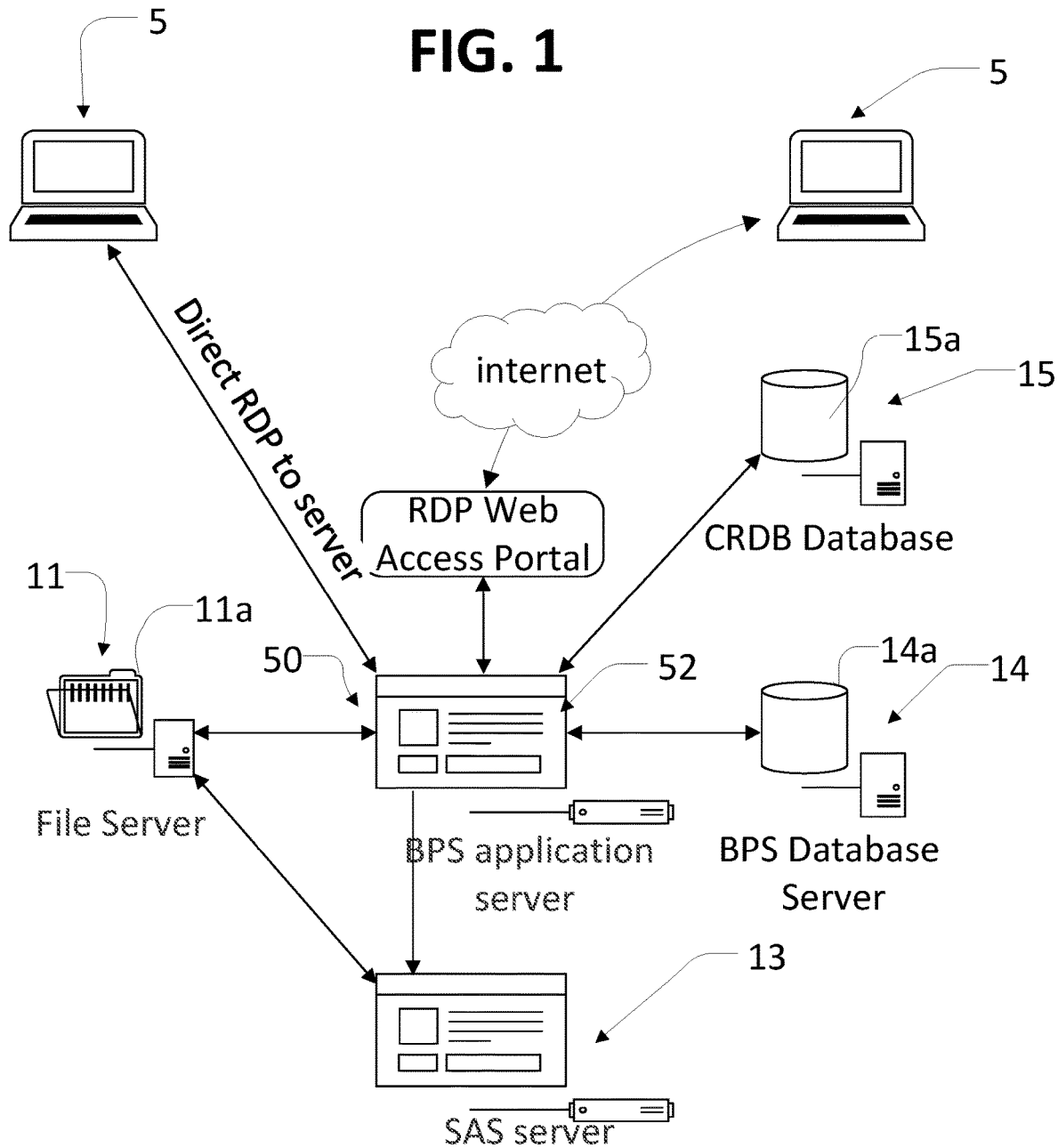

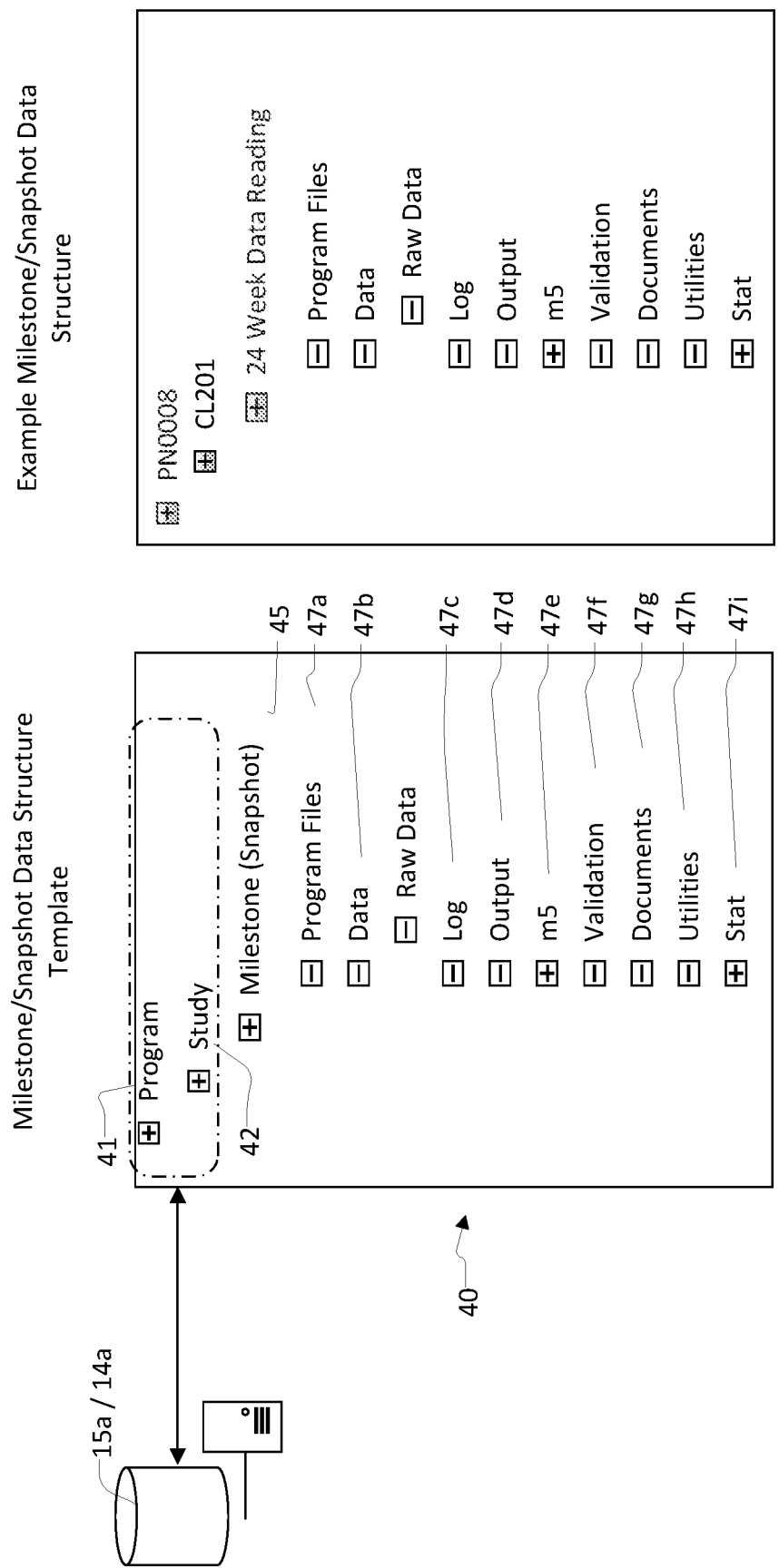

FIG. 2C

| Date | Oct 1, 2010 |
|---|---|
| Time | 10:00 am |
| By whom | BPUser1 |
| What is changed | SAS file p1.sas Status |
| Value before change | In Development |
| Value after change | Ready for Validation |

| | |
|---|---|
| | Nov 2, 2010 |
| | 1:30 pm |
| | BPSAdmin |
| | BPSUser2's access to milestone folders |
| | Editor access |
| | Read access |

32a

| | |
|---|---|
| | Nov 6, 2010 |
| | 11:00 am |
| | BPuser3 |
| | Validation folder |
| | 2 files |
| | 3 files added qc_hm.sas |

Update Program File Attributes

| | | |
|---|---|---|
| SAS Program File Names*: | l-ae.sas | ← SAS File A |
| Description: | Lists all adverse events in decreasing date order | ← A-des |
| Program Types: | Planned | |
| Output Types: | Listing | |
| Due Dates: | 2018-03-30 | |
| Priority: | 1 | |
| Source Programmer: | bpsuser1 | |
| QC Validator: | bpsuser2 | |
| Validation Type: | Level 2 | |
| Lead Programmer: | bpsuser4 | |
| Status: | Ready for validation | |
| Open CDISC Checked: | | |
| Output Folder: | C:\TEMP\BPSWS\PN0002\201\36 Week Dat | ← A-out |
| Specifications Folder: | C:\TEMP\BPSWS\PN0002\201\36 Week Dat | ← A-spec |
| Source Input Files: | adae.sas7bdat<br>adsl:sas7bdat | ← A-s1, A-s2, ... |
| Comments: | This is my comments | ← A-com |

A-md1, A-md2, ...

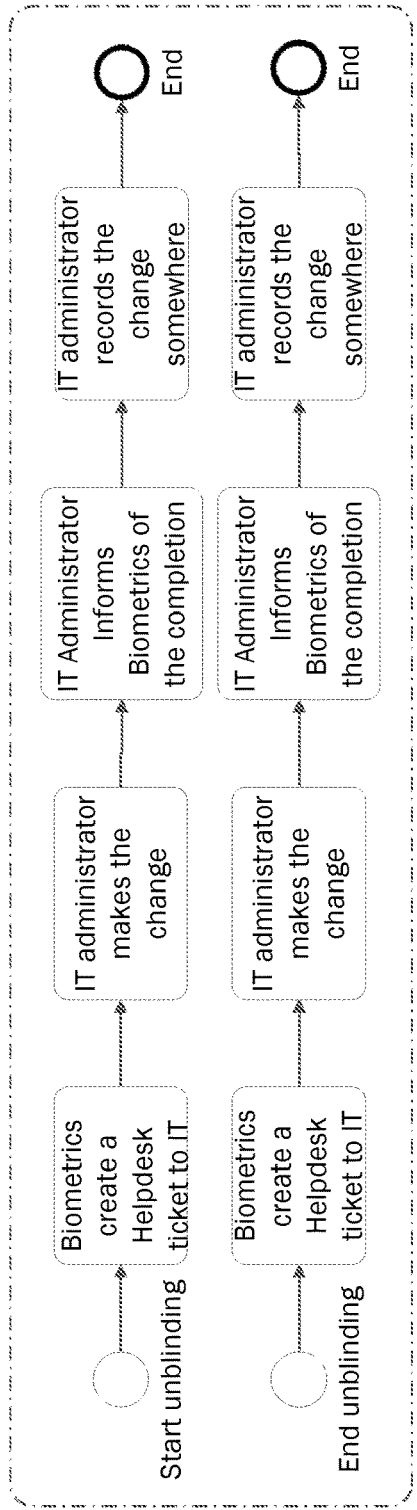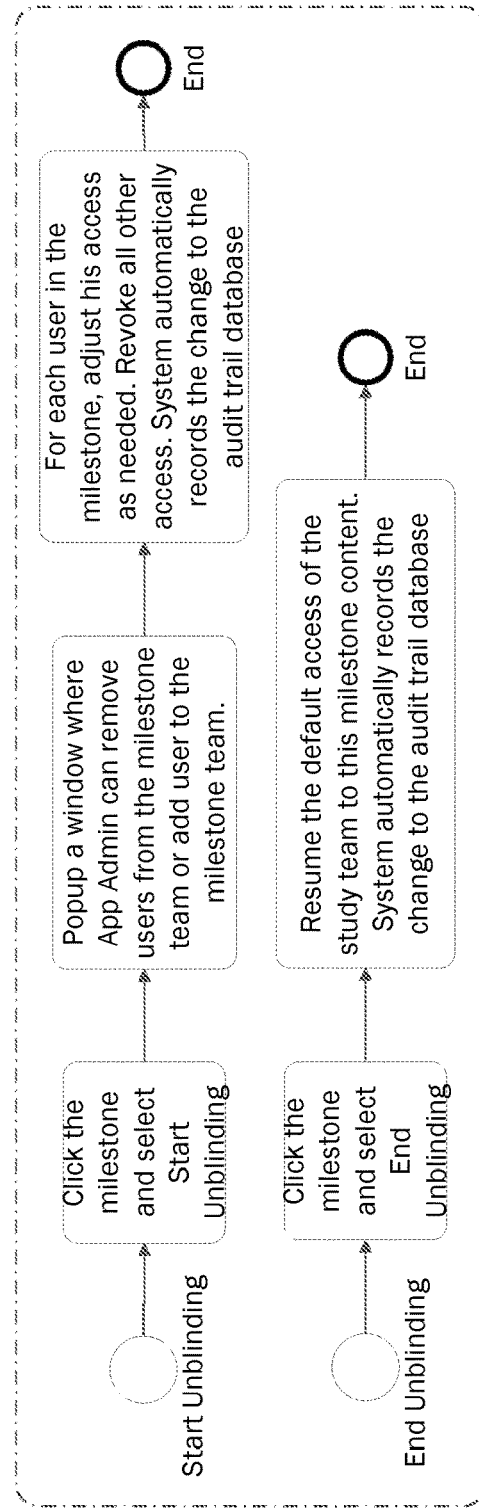
FIG. 3A (prior art)
FIG. 3B

SYSTEM AND METHOD FOR MANAGING A WORKFLOW FOR BIOMEDICAL DEVELOPMENT

BACKGROUND OF THE INVENTION

Field of the Invention

The present invention relates to a computer system for managing a workflow associated with a statistical analysis; more particularly, this invention relates to a biostatistical programming system used to a support a statistical analysis of biomedical data.

Description of the State of the Art

Biostatistical programming is a must-have function in biotech/pharmaceutical companies. The statistical data is used to determine if the therapy is safe and has the statistically meaningful efficacy. The SAS programming language is used for biostatistical programming. SAS and SAS server is described more fully in Base SAS® 9.4 Procedures Guide, Seventh Edition, Mar. 16, 2018. SAS OA, which is configured to run as a WINDOWS or LINUX desktop application and is the de facto software for the life science industry for biostatistical programming (BP). However, there is a significant gap between the functionality provided by SAS OA and the validation requirements for a biostatistical analysis (BA) of biomedical data for a regulatory agency, such as the FDA as defined under 21 CFR Part 11 or EU Annex 11, due to limitations in both a WINDOWS SAS or LINUX SAS environment. Moreover, SAS itself is a generic tool for computing and reporting results from a statistical analysis and offers very little in terms of project/process management, especially that meeting the needs of a life science industry.

The SAS Institute offers a web SAS server for drug development, called SAS DD. However, there are several drawbacks to the web SAS server. As a result, very few companies have adopted it as a tool for managing a workflow involving a BA of biomedical data, e.g., data collected during a single or double blinded clinical study. The BA analysis method and working files employed during the workflow are often subject to validation and reporting requirements to regulatory agencies, which makes the organization, cooperation and coordination among persons having different specialties within a life science company (e.g., statistics, programming, and agency regulations) complex and highly interactive during the course of the workflow.

Indeed, the challenges in managing a workflow of biomedical information for a life sciences company are unique, not only because of the reporting and validation requirements, time-sensitive nature of the completion time and highly sensitive nature of clinical data used for the BA. A wide spectrum of professionals with specialized knowledge and different priorities need to cooperate and coordinate their respective tasks during the course of the workflow in order to ensure a successful completion in an efficient manner.

U.S. Pat. No. 7,970,630 to the SAS Institute describes an integrated biomedical information portal system. This system is a web-based application for organizing biomedical information. The portal system has a database that stores data collected from biomedical development phases, meta-data data structure that describes data collected during a biomedical development phase, and at least one graphical user interface that collects data during the biomedical development phase. The system described in this patent fails to address several unmet needs as summarized above. Moreover, it is a web-based application, not a desktop application.

In view of the foregoing, there is a need for a system for managing a workflow for biomedical development that can address the special needs of a life science company arising during the course of a workflow.

SUMMARY OF THE INVENTION

A biostatistical programming studio (BPS) according to the invention meets one or more of the foregoing needs of a life sciences company during the course of a workflow for biomedical information. The BPS according to a preferred embodiment is a software based system running in a desktop environment, e.g., using a WINDOWS or LINUX operating system, as opposed to a web-based system that requires a web browser to execute an application. The BPS works on top of an SAS system running in the desktop environment, and provides the needed file and data management, traceability and record keeping required for satisfying validation requirements, e.g., the 21 CFR Part 11/EU Annex 11, when submitting biomedical information from a BA to a regulatory agency. In addition, the BPS automates many processes and greatly improves efficiencies in the workflow among different life science professionals having different specialties, responsibilities and priorities within a life science company, e.g., source programmer, validation programmer, lead programmer, biostatistician, data management and regulatory specialist.

The BPS according to the preferred embodiment provides an interactive graphical user interface or GUI. The GUI allows a person with access rights to edit, create, modify and communicate messages to members of the workflow concerning a SAS program file. Information such as specification files, input files, output files, version number and status for a SAS program intended for use in a BA is made available to a user through the GUI, provided the appropriate access rights have been given.

The data and output management and database system (accessed by the GUI), provides greatly enhanced communication, coordination and efficiency among the biostatistician, programmer, regulatory specialist, and information technology/data management during the course of a workflow for biomedical information. Typically, when completing a BA for a milestone event, a life science company employs all these professionals during the course of a workflow directed to completion of a task, e.g., submission of a new drug application (NDA), report an adverse event or efficacy from clinical or pre-clinical data.

The invention overcomes an existing practice, widespread throughout life science companies, of different programmers or data specialists maintaining separate files and folders of input and output files, which output files are often dependent on input/output from another programmer or another data specialist assigned to the workflow. Version control and traceability is very difficult to maintain. Personnel assigned to the workflow create many layers of folders requiring separate programs to access or control the use of input and output files. Indeed, it is not uncommon to find that within the same life science company, the structure of folders and file management can be different from study to study, or there is no fixed folder structure, or templates for organizing files in a logical order suited to the special needs of a life science company for all BA workflows in support of a study milestone. While it may seem like a straightforward task to make this system more efficient and solve these problems, it is not because of the special needs and wide spectrum of professionals with different priorities that contribute to the workflow.

Related to these needs, the invention overcomes the problems of creating and managing several layers or folder structures that contain the same information. The BPS may require only two layers of folders and associates each folder in a file share with a set of pre-defined metadata in a database, thereby linking or associating information between or among files that share data. For example, if the output from one SAS program is the input for another SAS program, which is very common, a common practice in the art is create another subfolder and manually copy output of one program into the input folder of another program. The invention embodied in the BPS improves on this prior art method by incorporating into its folder structure the associated inputs/outputs and logically separated by data type. This standard brings uniformity and simplicity across all studies, and makes obstacles like the WINDOWS 260-character path limit issue less a concern. In addition, the BPS employs a global variable called workspace root directory, whose value is defined and can be changed in an "Admin" page. This allows the company to change the root directory to anywhere, yet all the SAS programs still run without issue.

As mentioned earlier, SAS is the default software for data analysis in life science industry. The FDA and European Medicines Agency (EMA) themselves use SAS to evaluate a treatment. It is known that neither WINDOWS nor LINUX is fully compliant to the Part 11/Annex 11 rules, mainly because WINDOWS/LINUX by design doesn't have the capability to track metadata changes and keep versions, so the regulatory agencies require life science companies to record these using other tools, e.g., a spreadsheet program. For example, if programmer A creates a SAS program called p1.sas that produces 4 outputs O1, O2, O3, and O4, Programmer B is assigned as the validation programmer for this so he created 3 validation programs, v1 to verify O1, v2 to verify O2 and O3, and v3 to verify O4. If all are correct, p1.sas will be promoted to an In-Production status. Days later, it was found that p1.sas no longer runs without error, or produces wrong results. At this point, workflow participants typically ask two questions: who changed it? How can I get the In-Production version back? WINDOWS metadata does not store information to answer these kinds of questions. Although MS Office products like WORD, EXCEL, POWERPOINT, etc. have a last-modified-by metadata, for other types of file, no such information is recorded. Another, much bigger problem can arise when, for example, someone changes a SAS program after In-Production, which programming changes lead to a false indication that a treatment has very good efficacy and the result is then publicly announced (the company's stock price skyrockets). FDA receives the application and writes their own SAS program to validate the results, and discovers that the modified program is a fraud. Upon the subsequent announcement of audit of the workflow, the company cannot rely on data kept/maintained by a desktop operating system such as WINDOWS or LINUX. This is a reason why the FDA requires that companies keep track of changes to programs/data using tools like a spreadsheet to record what actually happened (e.g., who did the source code review and when, who signed off on it, and who used the source code or output therefrom as input to other programs). Even with the help of this manual process it only partially mitigates the problem to some extent. For example, people may forget to record a change, and recorded changes can be changed without an audit trail recording such a change. An ideal audit trail systematically record all changes and once recorded it is not allowed to change.

Resolving the audit trail problem is one important, but not the only important aspect of invention. A Biometrics department of a life science company usually has three functions contributing to the BA of the milestone:

Biostatistics (design the study, how many patients needed, how many visits, what percent are placebos, what data points need capturing during each patient visit, what Table, Figure, Listing is/are needed to check efficacy or safety, etc.), Statistical Programming to write the programs to produce what the Biostatistics want (subject to change during the workflow); and Data Management to design CRF forms for clinicians to collect data during patient visits or lab work.

There are different dynamics among these functions in different companies, typically counter-productive because the individuals involved having different specialties, needs and priorities than others in the workflow group. For example, a statistician may take the output from a program that is work-in-progress and has not reached the In-Production stage yet, and share it with the project team. He does so for reasons including claiming credit and tight timeline, etc. The programmer can be annoyed by that since the program is not in the final version yet. The BPS according to the invention addresses these types of problems that are unique to the life sciences industry can create reduce or obviate these conflicts by employing a flexible In-application/in-production permission management system. For efficiency, sometimes, a programmer finishes her job but does not immediately inform other programmers and a lot of time wasted in waiting. Using the BPS, now when the status changes, an email notification is sent automatically. Or an In-application IM can be used to communicate.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

BRIEF DESCRIPTION OF THE DRAWINGS

FIG. 1 is schematic diagram showing a biostatistical programming system (BPS) for managing a workflow space of a workflow relating to biostatistical analysis of biomedical data.

FIG. 2A is a schematic diagram of a graphical user interface (GUI) and data structure associated with a milestone (also called a snapshot) of a clinical study, which is stored and accessed by the BPS of FIG. 1 during the course of a workflow.

FIG. 2C is an example of a data structure of a record of the audit trail records from FIG. 2B.

FIG. 2D is a GUI for a SAS program and its associated metadata accessed during the course of the workflow. The SAS program and associated metadata depicts the contents of one of the records stored among the records depicted in FIG. 2B.

FIG. 3A is a prior art method for blinding and unblinding clinical study data in relation to a milestone biostatistical analysis (BA).

FIG. 3B is a method for starting or ending unblinding clinical study data using menu commands available from the GUI of FIG. 2A.

DETAILED DESCRIPTION

Figure 2B:
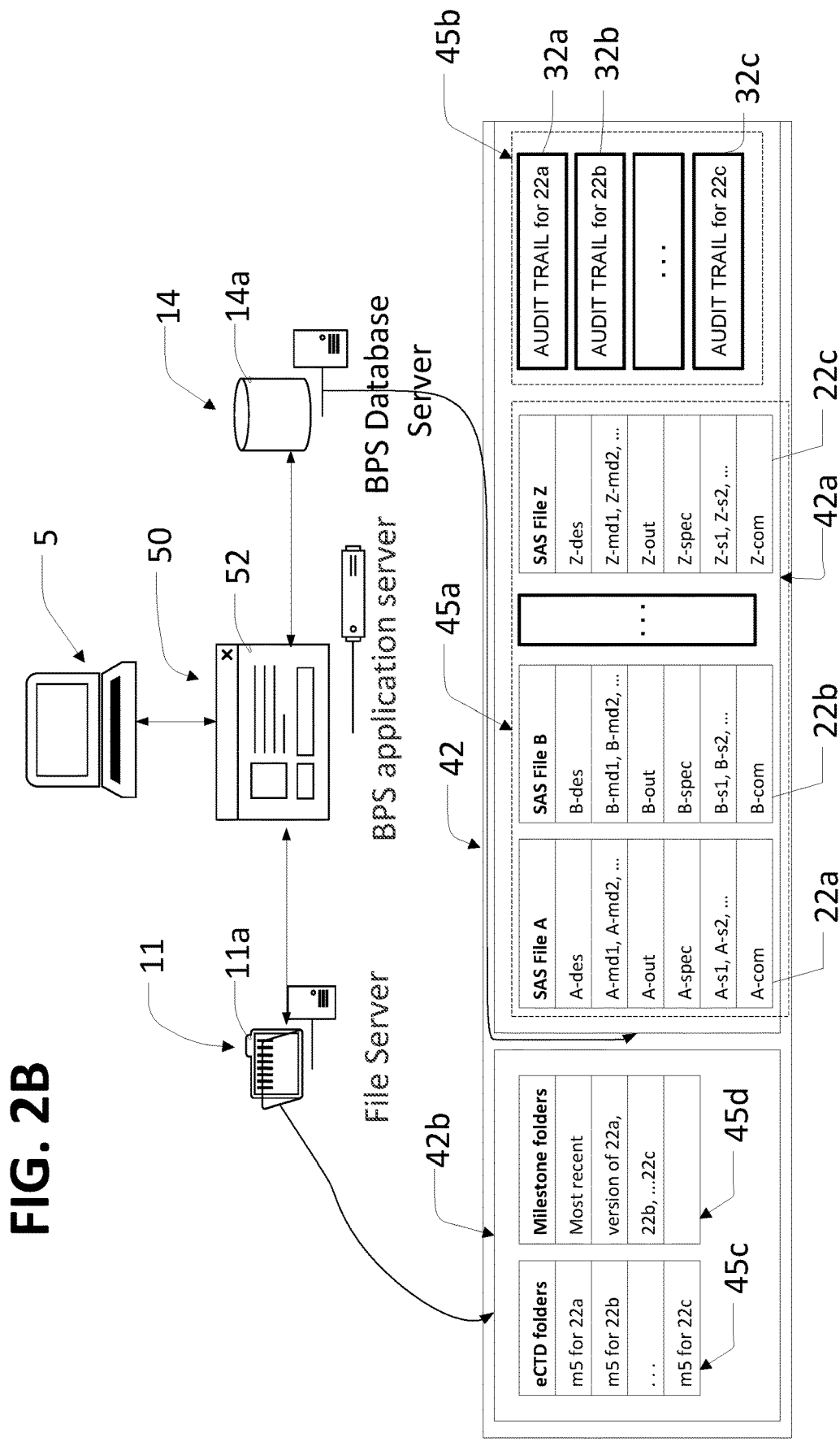
FIG. 2B is a schematic diagram showing how SAS program files and associated metadata work, which are generated or accessible from the GUI of FIG. 2D. The SAS program files are stored in a file server and its metadata are stored in a SQL database of FIG. 1. Also shown are audit trail records stored for the programs and metadata used/changed during the course of the workflow using the BPS of FIG. 1.

In the description like reference numbers appearing in the drawings and description designate corresponding or like elements among the different views.

For purposes of this disclosure, the following terms and definitions apply:

Module 5 (m5) of eCTD, m5 compatible folder or file format referred to herein means the commonly agreed upon format by the ICH for the preparation of a well-structured electronic Common Technical Document (eCTD) for applications that will be submitted to regulatory authorities. The format concerning statistical analysis of biomedical data is defined in module 5 (m5) of eCTD. This format and its requirements are defined in INTERNATIONAL CONFERENCE ON HARMONISATION OF TECHNICAL REQUIREMENTS FOR REGISTRATION OF PHARMACEUTICALS FOR HUMAN USE, ICH eCTD Specification V 3.2.2, 16 Jul. 2008.

The Analysis Data Model (ADaM) document specifies the fundamental principles and standards to follow in the creation of analysis datasets and associated metadata in connection with a BA of biomedical data. The ADaM is described in Analysis Data Model (ADaM), CDISC Analysis Data Model Version 2.1 (prepared by the CDISC Analysis Data Model Team), Clinical Data Interchange Standards Consortium, Inc., Dec. 17, 2009.

Study Data Tabulation Model (SDTM) defines a standard structure for study data tabulations that are to be submitted as part of a product application to a regulatory authority. The SDTM format is described in Study Data Tabulation Model (version 1.5) (prepared by the CDISC Submission Data Standards Team and CDISC SDTM Governance Committee), Clinical Data Interchange Standards Consortium, Inc., Dec. 17, 2009.

21 CFR Part 11 outlines the FDA rules on electronic signature and electronic records for all FDA regulated products. Audit history including versioning is part of the requirement on maintenance and use of electronic records. Annex 11 is the European Union's (EU) counterpart to US 21 CFR Part 11.

Biomedical data includes data acquired from basic medical research, pre-clinical research and clinical research.

A "workflow" is a sequence of administrative, programming, and validation steps undertaken to perform a biostatistical analysis (BA) for reporting statistics about biological outcomes occurring during the course of a clinical study. In the preferred embodiment the workflow is organized, managed and run by a biometrics department of a life science corporation, which may use results from the BA to submit filings to a regulatory agency in connection with seeking approval for a new drug or medical device, or for other reasons. The workflow may use data from animal or human clinical trials. The BPS according to a preferred embodiment of the invention, FIG. 1, provides a desktop workflow space or studio for managing/running a workflow associated with a BA of biomedical data from a milestone event.

A "milestone" or "snapshot" is period of time in which biomedical data is collected during a clinical trial and a biostatistical analysis (BA) is made to evaluate the efficacy and/or safety of the treatment to this point. Unless stated otherwise, a workflow according to the invention means a BA workflow in connection with a milestone or snapshot event during a clinical trial where biomedical data is generated and results recorded, which can be used for reporting to a government agency. A workflow according to the invention may include the setup, file management, BA and all data relating to the BA needed for reporting to a government agency and/or needed to maintain an audit trail in the event the government agency audits the entity running the clinical study and reporting the results in connection with, e.g., a new drug application or NDA.

A "biostatistical programmer" (BP) is a person who performs statistical analysis (SA) on biomedical data, such as SA on clinical data reported during a milestone or snapshot of a clinical trial.

FIG. 1 shows the server architecture for a Biostatistical Programming Studio (BPS) according to a preferred embodiment. A user 5, such as a "biostatistical programmer" (BP) may access a BPS application 50 of the BPS, which provides a remote desktop graphical user interface 52 that runs on a server. Application 50 is accessed and controlled by user 5 through a remote desktop program (RDP) connection through a local area network (LAN) wired or wireless, or over the internet. User 5 can access BPS via RDP directly, or access to a web portal where the remote server application 50 is published.

The application 50 is a desktop application, e.g., an application that runs on a WINDOWS or LINUX based operating system, as opposed to a web-based application where access to the application through a web browser, or mobile application, where the app is specifically designed for mobile devices. For example, the application 50 can be installed in a Windows server or a Linux server, depending on which operating system the SAS was installed. File server 11, SAS server 13, application server 52a, and database server 14 can reside on the same physical or virtual machine.

The BPS interacts with files and directories 11a located on server 11 and metadata and files on a database 14a or the central reference database (CRDB) database 15a located on server 15; BPS allows users to run SAS programs without opening them in SAS; however, when opening a SAS program file, it will be opened in SAS by default, where users can make edits and run directly on the SAS server 13. The SAS workspace is maintained in the file system on file server 11a, including a structure from root to Programs, studies, milestones, and all the way to the individual files (see FIGS. 2A, 2B and 2D). The metadata and all versioned files from the workflow are maintained in the database 14a.

Application 50 presents the user 5 with a workflow space including graphical user interface (GUI) 52, which has a series of drop-down menus used to access/organize files, personnel who will contribute to the workflow, data access rights, reports, etc. for new workflow creation, or to manage existing workflows (the entirety of the data, folder structure, and system of drop down menus accessed through application 50 will be referred to as the workflow space). Some of the features of this workflow space include creating and tracking changes for SAS programs within an existing workflow, assigning access rights to single or double blinded studies, updating an existing workflow or program, making program changes and recording and reporting results from a biostatistical analysis of biomedical data. The application 50 running on server 52a runs on top of a SAS server 13. The SAS server 13 and SAS running on this server provides the programming environment for running SAS programs, library files for formatting data, plots, lists, statistical computations, etc. in the application 50 environment for purposes of performing a biostatistical analysis (BA) on one or more milestones or snapshots of a clinical trial.

Application 50 may be configured to run with SAS and SAS server through an API, or by calling SAS as a program complied separately from application 50, e.g., calling SAS via a command line in WINDOWS or using shell scripts in LINUX.

The application 50 is connected to memory accessed through a file server 11 for storing data associated with a workflow. File server 11 provides read and write access to non-volatile memory 11a. Application 50 is also connected to a database 14a through a database server 14 and a Central Reference database 15a (CRDB 15a) that may reside in the cloud. Database server 14 provides read and write access to non-volatile memory of BPS database 14a, which stores metadata as well as versions of program files and outputs, as described more fully in connection with FIGS. 2A, 2B, 2C, and 2D.

In the preferred embodiment the BPS provides a workflow space, accessible using application 50, and used to assist a Biometrics department with performing a BA and organizing the data and programming aspects of the related workflow. It also has tools that allows the user 5 to transfer data from a prior study or milestone, give access rights to data collected during a clinical or pre-clinical study, and provide the files and data needed, in connection with reported findings, for electronic submission to a regulatory agency, e.g., the FDA or EMA. Each such study can have multiple milestones (also called snapshots). When a milestone is created (or duplicated out of an existing milestone), a fixed folder or data structure for the workflow is established in the file system 11a, e.g., a WINDOWS/LINUX file system and related metadata in the database 14a is created and associated with the files in the file system 11a, accessible to the user 5 through the workflow space provided by the BPS.

Referring now to FIG. 2A, there is shown a GUI 40 showing a set of drop down menus presented by application 50 to user 5 in connection with a new or existing workflow space for a biometrics group or department. FIG. 2A will be referenced to describe both the kinds of data represented in the directory structure shown in the GUI 40, and how to access, input, export, etc. data and information associated with a workflow using the workflow space provided by GUI 40. During the initial setup for the workflow, user 5 may be one or more members of a biometrics department. For example, a biostatistician, statistical programmer and/or data management person may use application 50 to initiate or contribute to a new workflow space accessible through application 50.

The drop-down menu system and data associated with a data structure organized under the workflow space 40 includes the following:

Program 41 is the root folder for accessing and selecting a clinical study under an existing program, e.g., drug program PN0008.

Study 42 is a folder or directory of one or more clinical studies, e.g., CL201 under program PN0008.

Figures 5A, 5B:
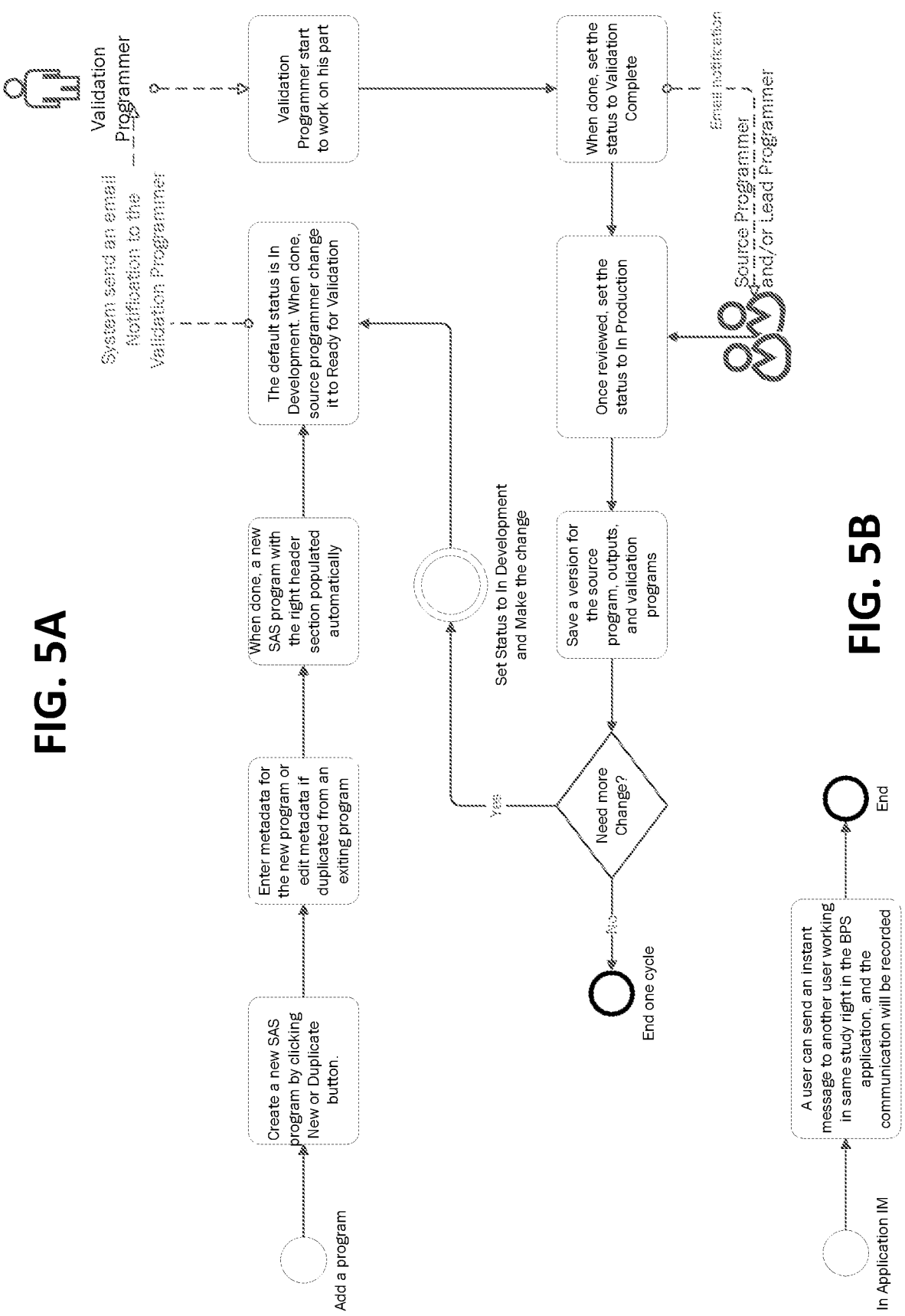
FIG. 5A is a flow diagram that depicts the creation, validation and approval process for a SAS program.
FIG. 5B depicts an in-application instant messaging system among programmers involved in the process of FIG. 5A to communicate when a program status has changed and any other matters associated with the workflow.

Under study 42 is the existing milestones 45. The user 5 may also create a new milestone 45. When a new milestone 45 is created, e.g., 72 week data or 36 week data, the sub-folders 47a through 47i are created automatically from scratch and there is no content in the sub-folders. When a new milestone is created by duplicating an existing milestone 45, the folder structure is copied over, and some pre-defined content from the existing milestone is carried over into the sub-folders of the milestone and the status of the program file is reset to in-development (FIG. 5A). Additionally, under the milestone 45 folder the user 5 may start unblinding or end unblinding, as explained in connection with FIGS. 3A-3B. A selection is made to either start unblinding data from a clinical study, or end unblinding.

Under programs 47a there are the programs previously used in the milestone, or empty if new milestone is being created. The programs include SAS programs executable using the SAS. These programs files are generated, validated, reviewed and revised during the course of a workflow, as explained in greater detail in connection with FIGS. 5A-5B. The view also allows programs used during the workflow to be converted to the appropriate file format and copied into the m5 folder (FIG. 2E).

Biomedical data or data 47b, which may be clean in standard format or noisy/raw data. The data 47b may be data from prior milestones along with new data from the clinical trial and within the new milestone 45, e.g., 24 week reporting milestone period for milestone 45 included with data from the 12 week milestone. From this menu data or raw data can be imported into the workflow space. The view also allows relevant data (STDM and ADaM) to be exported to the m5 folder and the list and attributes of the data files to be exported into a spreadsheet.

Log files 47c, which tracks what programs were run and when, and collects messages about the processing of SAS programs and any errors that might occur.

Output 47d, which are the output files from the BA programs run, e.g., table, listing, or figures, etc.

m5 47e, which houses all the data relating to the BA for the milestone 45 as the required components from BA in m5, which regulatory group electronically submits to regulatory agencies along with other components of eCTD (e.g., m1, m2, m3, m4, etc.). This information is used by the regulatory agency to reproduce and verify all findings reported in the BA reports.

Validations 47*f*, which contains all validation or quality control (QC) programs. Each validation program QCs one or more of the outputs from the corresponding source programs that require Level 2 or Level 3 validations during the workflow.

Documents 47*g*, which are all documents related to the workflow process and BA. The documents are automatically reformatted (as needed) and copied into the m5 folder.

Utilities 47*h*, which stores all SAS Macros for the workflow. From within this folder one can also create macros used during the course of the workflow.

Stat 47*i*, which are all documents relevant to this milestone that statisticians involved in this milestone put there. The folder stats 47*i* also has a sub-folder called production output, which shows all in-production output files. This information is used by statisticians for making statistical inferences based on the BA.

The storage system part of the BPS provides file storage, organization, logging, and indexing to a desktop studio or workspace operating on a desktop application, e.g., WINDOWS or LINUX based operating system. The BPS is adapted for bringing electronic data associated with a BA and reported to a government agency in compliance with regulations, e.g., 21 CFR Part 11/EU Annex 11. Additionally, the BPS file system is constructed to automate many processes and creates efficiencies in a workflow between, for example, a source programmer and validation programmer and the lead programmer. As mentioned earlier, a desktop operating system such as WINDOWS or LINUX do not provide much metadata and track changes functionality for files. WINDOWS and LINUX have some version capability, but it is limited and not sufficient for complying with 21 CFR Part 11/EU Annex 11.

The workflow space includes the creation, review, and validation of SAS programs that are used to perform the SA/BA on the clinical data. The application 50 provides a GUI and set of drop-down menus for creating, editing and associating metadata for each program used during the workflow. An example of the GUI 54 is shown in FIG. 2D.

Figure 2E:
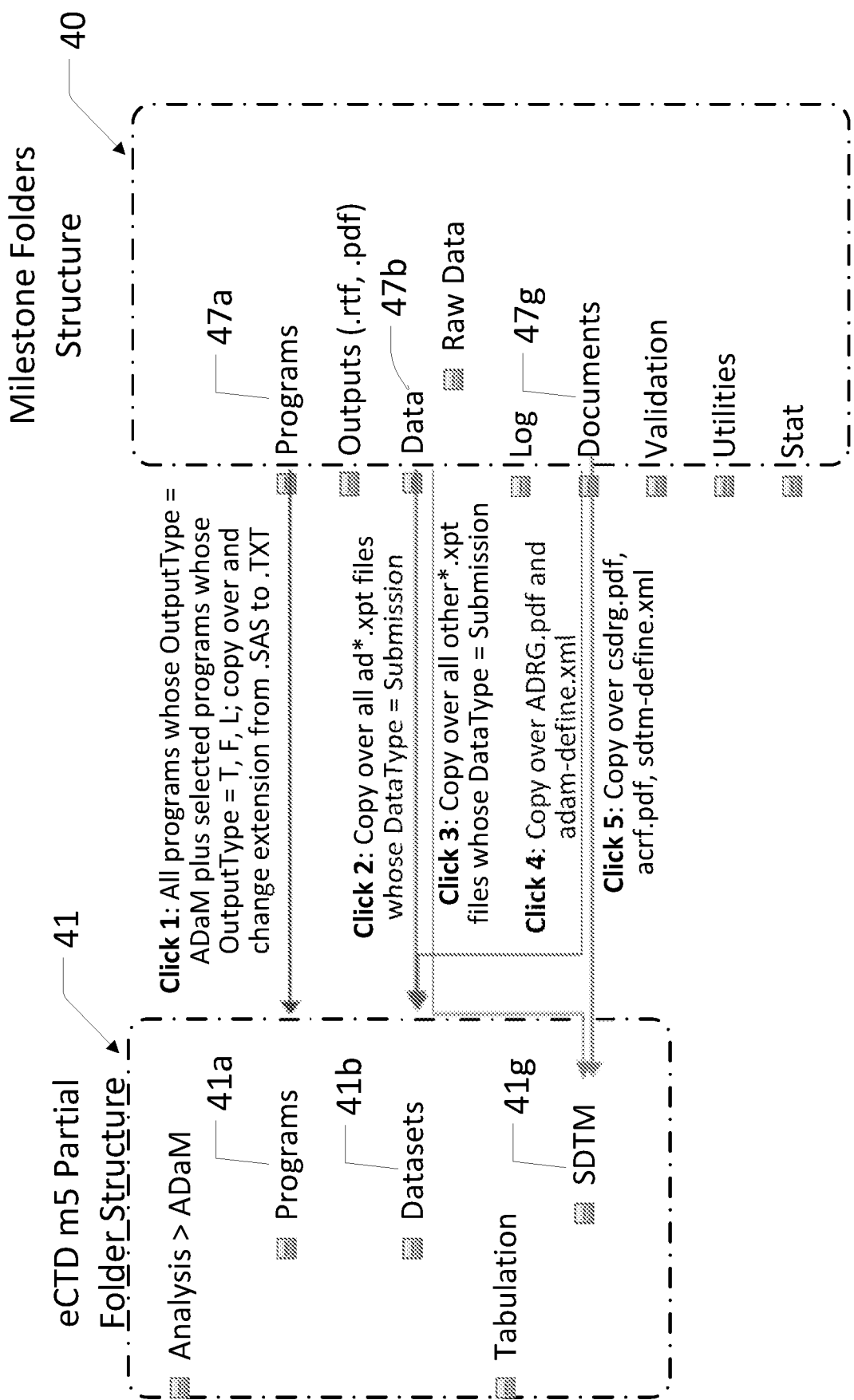
FIG. 2E is a schematic diagram illustrating how menu commands provided in the GUI of FIG. 2A can be used to push data and program files automatically and in correct format to an m5 compatible folder for submission to a regulatory agency.

FIG. 2D illustrates a GUI 54 relating to the management, control, edits and resources used by a SAS program. In this example, the SAS program has a filename "I-ae.sas" and is used to list all adverse events that were detected during the course of the milestone 45. The metadata associated with this SAS program is shown in TABLE 1:

TABLE 1 metadata associated with SAS program used during workflow (FIGs. 2B and 2D)

| Metadata type | description |
| --- | --- |
| SAS-file-A "SAS Program File Name" | Name of file and location for execution by SAS 13 |
| A-des "Description" | Text description of program function(s) |
| A-md1 "Program Type" | Status of program (planned, in development, or in production) |
| A-md2 "Output Type" | Type of output produced by SAS program |
| A-md3 | Date when program |

TABLE 1-continued metadata associated with SAS program used during workflow (FIGs. 2B and 2D)

| Metadata type | description |
| --- | --- |
| "Due Date" | validation needed, if any |
| A-md4 "Priority" | Priority level for program |
| A-md5 "SAS Programmer" | Name of assigned SAS programmer |
| A-md6 "QC Validation" | Name of assigned SAS programmer conducting validation of SAS-file-A |
| A-md7 "Validation Type" | Level of validation needed for SAS-file-A (Level 1-3) |
| A-md8 "Lead Programmer" | Name of Lead programmer |
| A-md9 "Status" | Indicates whether program in development, ready for validation, in validation, validation complete, or in production |
| A-out "Output folder" | File location where output files from SAS File A |
| A-spec "Specifications folder" | File location where Specifications for code in SAS File A |
| A-S1, A-S2, . . . "Source Input Folders" | Data files (input) files for SAS File A. |
| A-com "Comments" | User/programmer comments (text) |

An important aspect of invention is the associating of the SAS program, e.g., source code for a SAS program stored in a file called "I-ae.sas," in the file system with the metadata listed in TABLE 1 in database, not only when the SAS program file is initially created, but also when the metadata changes and/or any of the files associated from the program changes during the workflow. Whenever any of these changes takes place during the course of a workflow, the file and associated metadata are stored for later retrieval, and traceable as to version, person making the changes, when the changes were made and what were the associated input and output files in use.

There are, in general, three types of changes BPS tracks and records in connection with a SAS program used in the workflow, TYPE 1: changes to the metadata, but not the contents or files that the SAS program uses, or the SAS program. For example, the validation level or program status (e.g., Level 1 validation and status in production) is metadata that is often changed during the course of a workflow. Also, comment or text boxes a-des and a-com.

TYPE 2: changes to one or more of the files used by the SAS program or defining the SAS program attributes, or source code specification files; and TYPE 3: changes to the SAS program.

FIG. 2B is a schematic that will be used to fully explain how BPS stores SAS program file and related metadata information. First, it should be noted that during the course of the workflow there are many SAS programs created and potentially many versions of the program and related validation programs created and used. The file system 11*a* accessible through the server 11 and the database 14*a* hold all information used and produced during the workflow and available in the workflow space in memory 42, which in the preferred embodiment comprise separate memory.

Records 22a, 22b and 22c hold the SAS program files and associated metadata, input and output files, and specification files described above in connection with FIG. 2D in database 45a. The most recent versions of records 22a, 22b and 22c are stored in file system 11a memory 45d. The application 50 accesses the most recent versions of 22a, 22b, 22c located in memory 45d when writing and formatting data for the eCTD folder using application 50. Memory component of 45c of memory 42b stores the portions of this version of records 22a, 22b and 22c needed by the regulatory group and formatted for immediate use (m5 format). As a SAS program record 22 is updated or changed and a new version created, the prior version of record 22 in memory 45d is replaced. All versions of record 22 used during the course of the workflow are maintained in memory 45a. Memory 45b of database 45a stores audit trail records 32a, 32b and 32c associated with each of records 22a, 22b and 22c, respectively. The audit trail records 45b are maintained in the event that discovering who made what change to a record becomes necessary, or an audit of the company is called for by regulatory agency to which BA results were provided by the regulatory group (e.g., relating to a NDA).

The SAS program records 22a, 22b and 22c indicated in FIG. 2B use the same nomenclature as used for the metadata and files in record 22a corresponding to FIG. 2D. All information, including the file contents, locations and metadata associated with the file, are maintained in the records 22a, 22b, 22c so that the SAS program and everything pertaining to the SAS program, its use, revisions, output etc. can be instantly recalled and kept track of during the workflow and accessible via application 50 in the workflow space provided by BPS. The records 22b and 22c refer to different program files and associated metadata from record 22a, but having the same data structure as 22a. The different files and metadata for records 22b and 22c are indicated by the letters "B" and "Z" respectively that precede each metadata type (the record 22a is the same as that referred to in FIG. 2D in connection with "SAS File A"). These files in, or referenced in each one of the records 32a, 32b and 32c may share the same source or input files. This shared information is accessible traceable in either file paths or the metadata. For each of records 22a, 22c and 22b there is a separate pull-down menu system, as previously described for GUI 40. The content of the records 22b and 22c, like record 22a, are modified through a GUI structured in the same way as GUI 40. The metadata associated with the files may include a version number and the two versions may be accessible in the same record. For each record 22a, 22b, 22c in metadata and files 45a there is a corresponding GUI 40 available for accessing the records, and modifying, updating etc. the records.

Audit records 45b hold records 32a, 32b, 32c, which provide the information needed for auditing a work history, modifications, output etc. for each of the records 22a, 22b and 22c, respectively, during the course of the workflow. The generation of audit records 32a, 32b, etc. during the workflow addresses the need for an audit trail of a workflow in connection with a m5 folder accompanying a filing with a regulatory agency. In the case of the United States, the need for an audit trail is explained in *Guidance for Industry Part 11, Electronic Records; Electronic Signatures—Scope and Application*, August 2003. The audit trail is also needed to trace who made changes to programs, when and what kind of change, etc. to understand results or trace errors (as explained earlier).

Each of records 32a, 32b, 32c are automatically updated whenever any activity takes place involving one of the corresponding SAS program files, data, documents, validation, such as permission or other metadata changes, or a change to the SAS TOC. The audit trail records 32a state before and after a change happens to an electronic record. For example, record 32a containing an audit trail for record 22a may contain rows of data corresponding to each date and time when some activity involving the record 22a took place. For example, referring to FIG. 2C, the audit trail record 32a may have recorded activities taking place on Oct. 1, 2010, Nov. 2, 2010, and Nov. 6, 2010, involving BPUser1, BPSAdmin and BPuser3, respectively. The change made at each time, for example, may be a change to the SAS program file, its validation status (e.g., in production or in development), a change from editor access to read access (only) or when a new output file is created or the SAS program run to produce the output file, respectively. The audit trail may also indicate where the files are located and whether or when any of the files were opened or accessed by another program, again as a separate record, with a time and date stamp. Access to the audit trail records 45b is strictly limited to a BPS application administrator.

Figure 2F:
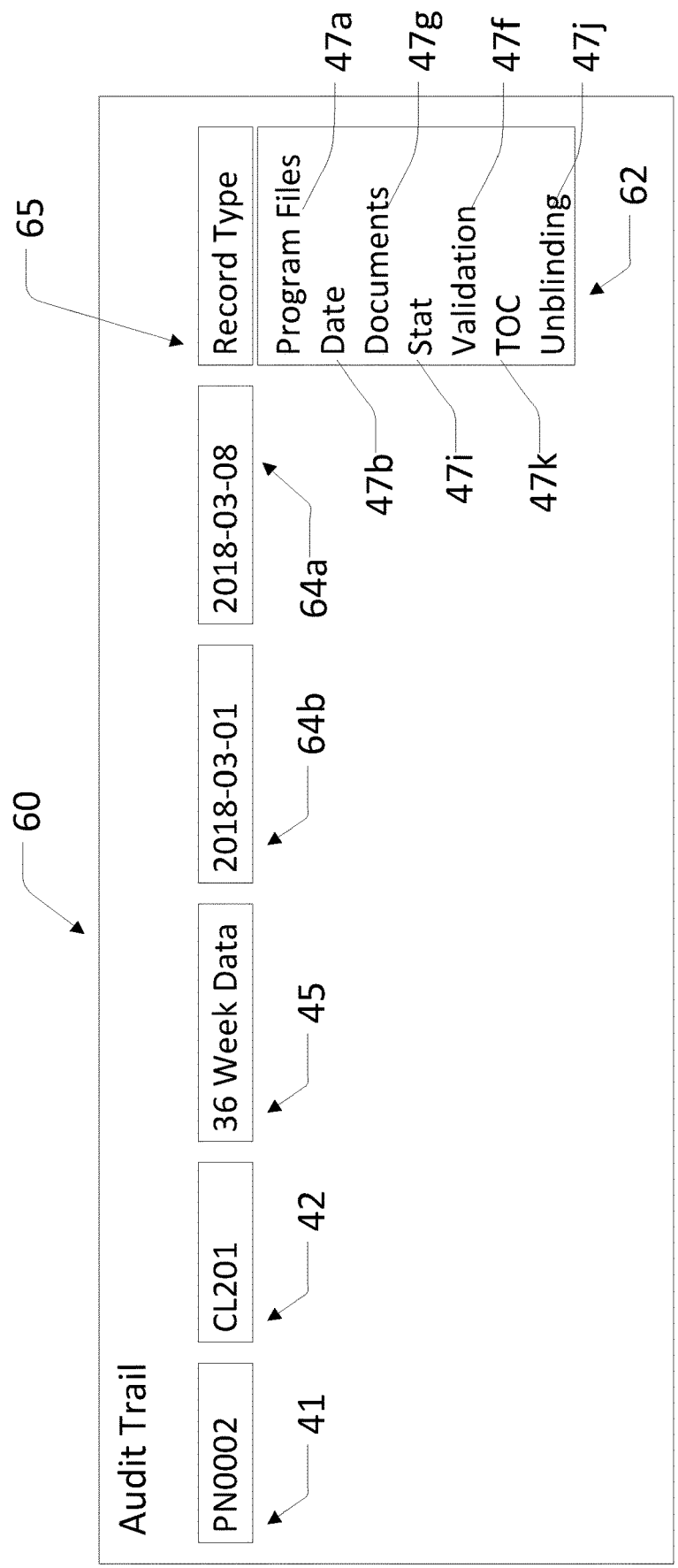
FIG. 2F is a GUI depicting a GUI for accessing information contained in audit trail records.

FIG. 2F depicts a GUI 60 for accessing information found in an audit trail record 32. The GUI shows the audit trail record can be accessed under the program 41, study 42, milestone 45 and limited to a start date 64b and end date 64a. Under menu selection 65 the user may further select the particular (sub) record or sub-folder for which the audit inquiry is requested, or view the audit history over the date range for all categories 62 of the audit trail record 32 associated with record 22.

The machine instructions executed to provide the various forms of functionality described herein, may include several modules each have different functions as described above. The code used to provide the audit trail tracking, monitoring, audit trail records, for example, may be a separate module or part of the same module as the module(s) used for presenting the menu system and managing resources associated with application 50. In one embodiment an audit trail module may include or access resources provided or already from the database 14a of 15a, e.g., machine instructions compiled from SQL source code used to manage read and write requests. According to this embodiment the audit trail may operate during the course of the workflow by tracking, using the database resource, when any changes are made to one of the files or metadata within the scope of the audit trail, and when such a change is detected, reporting this event to a module that records the audit trail record with a time and date stamp, along with the information pertaining to the user making the change, the record, file or metadata that was changed (for example) using information available from the database resource or accessed from the application 50 module(s).

A SAS program that produces any output of the type Table, Figure, or Listing, will need as input information from a SAS TOC to produce the output. For example, if a SAS program is used to draw a table and populate it with data, it needs a table number, table title, sometimes a subtitle, footnotes, etc. Current industry practice creates a spreadsheet file that contains the SAS TOC information needed for a workflow under the milestone. SAS programs read the number, title, etc. information from this file. Typically the file is located on a file system and available to one user at a time. Thus, if one workflow participant is editing the file, the file is locked and no one else can edit it at the same time. Also, tracking when and what changes are made and by whom during the course of the workflow (during regulatory audit or to trace errors or unexpected results) is complicated for reason given earlier. The BPS solves both these problems. First, maintains a TOC file in database 14a, so that any number of users can work on it at the same time. The SAS program reads the most up to date TOC data even while it is being updated by another user during the workflow. Second, the audit trail records include an audit trail record (not shown) for a SAS TOC.

When an update or filing with a regulatory or government agency (e.g., the FDA), is needed, part of this submission is all the data files and programs used to produce the output biostatical results reported in the filing with the regulatory agency. This information is used by the regulatory agency to reproduce and verify the results reported in a company's submission. The required format for the data is eCTD m5.

According to another aspect of BPS the GUI 40 includes buttons that allow the biometrics group member, i.e., a BP, to send the relevant data to the m5 folder records 45c for each record 45a. BPS 10 allows the BP user of application 50 to push the data needed for m5 folder instead of having someone in the regulatory group of the company to seek out and include ("pull" instead of "push") the data into the m5 folder 45c and/or a biometrics group locating the correct files and formatting them in the absence of the data structure format provided by the workflow space of BPS. The application 50 automatically formats and stores the correct data files (latest versions stored in memory 45d) needed in the m5 folder through interaction with the GUI for access by the regulatory group. This feature is enabled by the structure of the data structure used for the SAS program files and associated metadata. The advantage of BPS includes only the current most recent versions of the programs (located in memory 45d), automatically accessed and stored in the correct format and in the correct locations in the m5 folder, as opposed to having someone outside of the biometrics group manually access the SAS data files, format them and determine where the respective files belong in the m5 folder.

Referring to FIG. 2E, the workflow space 40/data structure GUI 40 is shown in the right hand side. On the left hand side is the folder structure 41 for the m5 folder portion of an electronic submission under the eCTD standard format. The data for the m5 folder can be transferred from the drop-down menu options in the GUI 40 by clicking the send data to the corresponding locations in the m5 folder. When the user 5 clicks on Programs 47a all programs with the designated output type shown in FIG. 2E are first formatted and then transferred to the appropriate folders, as indicated. As little as five "clicks" of menu buttons are needed to provide everything from the workspace 40 that is needed in the m5 folder. The transfer process includes, as indicated, moving the files and data according to the type of output file that was generated or used during the course of the workflow and maintained in the workspace 40. In some cases, the files are converted as well:

programs 47a are transferred to the programs 41a part of the m5 folder and depending on the output type file extension/type is changed data 47b and documents 47g are transferred to the datasets 41b part of the m5 folder, depending on the file type as shown data 47b and documents 47g are transferred to the SD™ 41g portion of folder 41g Thus, with this automation built into the BPS there is a mapping automatically created when a new workspace is created and program files generated during the course of the workflow. When content is ready for a regulatory submission, a biostatistician can click a button to copy the right content in right format to m5. For example, the "Send to m5" button in Program Files view, upon click, will copy all source programs whose OutputType is ADaM, plus selected source programs whose OutputType is Table, or Figure, or Listing, change these file extension from .sas to .txt, and put them into the m5 Analysis>ADaM>Programs folder.

Referring to FIG. 3A and FIG. 3B, there are shown the steps needed to start or end un-blinding the milestone data according to existing (prior art) methods versus that used by application 50.

Most clinical trials are conducted not in open label (i.e., the placebo versus drug with active ingredient known to both patient and doctor), but instead are blinded (or double blinded), where participants (and the researchers) don't know whether the treatment/allocation received is a placebo or a drug. Un-blinding is the process by which these treatment/allocation details are made available to determine its efficacy and/or safety. Since whether a treatment is effective/safe carries significant economic value, it's always kept absolutely confidential. Only a few statistical programmer/biostatistician should have the access needed to make the evaluation.

Referring to FIG. 3A, the current practice is Biometrics group creates a helpdesk ticket to IT, telling them whose access should be maintained to which directory and whose access should be revoked. The IT administrator verifies with the management of Biometrics to validate the request, make corresponding changes, and then inform Biometrics of when the starting un-blinding permission change request is completed. IT administrator need to note what is changed and keep the record for potential audit. When the result becomes public, another request needs to be sent to resume access.

When using the BPS the starting and ending un-blinding process is handled by a series of windows in the GUI 52, as shown in FIG. 3B. Both processes can be performed by application administrator in BPS without resorting to IT, plus all the changes are recorded in the audit trail database 45b.

Figure 4A:
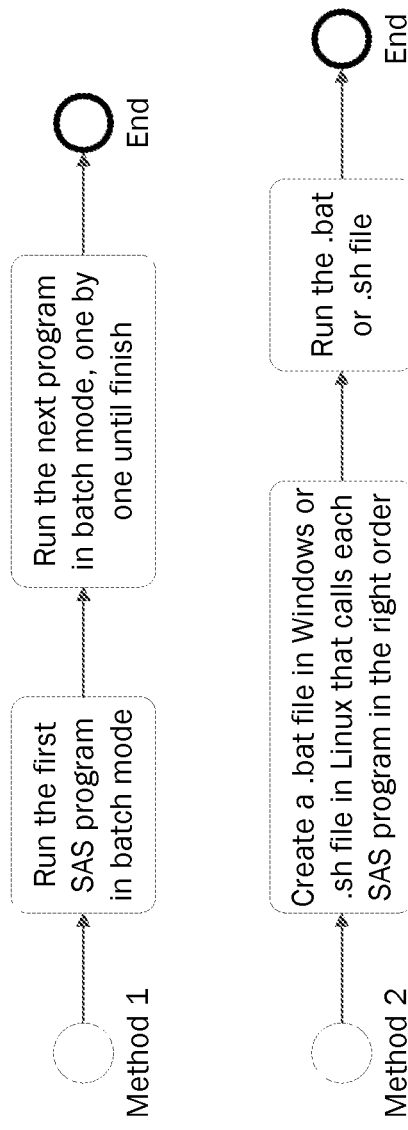
FIG. 4A depicts two prior art methods for batch submission of SAS program jobs.

During the workflow process, SAS programs may need execution in a particular order when the input to a SAS program is generated from another SAS program. Thus, if the output from a first SAS program is needed as input to a second SAS program, the first SAS program must be run before the second SAS program. FIG. 4A illustrates two prior art methods for running SAS programs in order. Either the programs are run one after another by the BP, or the order of execution is defined in a .bat or .sh file.

Figure 4B:
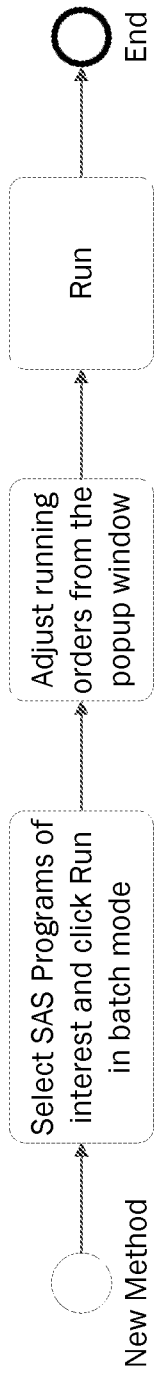
FIG. 4B is a method for batch submission of SAS program jobs using a GUI interface available from the menus in FIG. 2A.

FIG. 4B indicates the steps needed to run programs in a particular order using the application 50. Using a drop down menu, programs are selected and the sequence of execution designated using the GUI provided.

A SAS program used during the course of workflow typically involves three separate roles: source programmer, validation programmer, and lead programmer. The assignments to the specific one or more persons during the program creation, validation and use for a SAS program are defined and updated in the GUI 54 (FIG. 2D), specifically metadata md5, md6 and md8. Additionally, the GUI 54 includes metadata md7 that specifies the validation type for the program, e.g., from Level 1 (self-review & log check, no validation step needed) to Level 2 (Spot check and code review), or Level 2 to Level 3 (Independent replication of course code).

As explained earlier, the existing methods for creating, validating, updating and running SAS programs during a milestone workflow suffers from a number of drawbacks including delays, changes that were not tracked, updates to programs or programs being used that were not properly validated. According to another aspect of the invention, these drawbacks are overcome by leveraging metadata associated with a SAS program, in particular, by sending automatic messages to the programmers responsible for the SAS program, its use and correctness, updating the status with instant notification to other programmers working/using the SAS program (as defined in the GUI 54) and making all of these associations of record in the file system as explained earlier. This way, any changes can be easily tracked to the person, time and file versions.

FIGS. 5A and 5B depict a process for updating and tracking program development and use during the course of a workflow and reporting on progress/changes to collaborating programmers. Referring to FIG. 5A there is shown the process (from left to right) for adding a new program (or duplicating an existing program) and associating the metadata associated with the management of the SAS program using the GUI 54. The information is stored and maintained in a record 22a among the other programs and associated metadata in the workflow and the audit trail record 32a activated. At this point the record 22a and SAS program is created. The default status when a new record created (or existing one duplicated) is "in development" meaning that the SAS program needs to run and output reviewed by the SAS programmer. After the SAS program has reached a level of completion, the SAS programmer (md5) changes the application status in the GUI 54 from "in development" to "ready for validation." At this point the BPS automatically sends an e-mail or equivalent electronic notification to the validating programmer (md6). The validating programmer writes separate SAS programs that will produce all the outputs that the source program produced and then compare if the outputs match. In some cases, the validation programmer also visually checks the source SAS program by verifying that the libraries and functions being employed are correct for purposes of generating the correct statistics called for by the statistician involved in, or defining the workflow—i.e., that the mathematics are correct. This may involve generating one or more separate, validating programs such as when a Level 3 validation is needed for the SAS program.

When validation is complete the validation programmer changes the status in the GUI 54 from "in validation" to "validation complete" (md9). At this point another electronic notification, e.g., e-mail, is automatically sent to the lead programmer (md8) indicating that the SAS program is ready for final review. If the lead programmer is satisfied the SAS program status is changed in the GUI 54, either source or SAS programmer or lead programmer will change the program status to "in production." At this point the SAS program version is saved as a new record in records 45a and use of the SAS program in the workflow begins. Included with the record for the SAS program may be the validating programs and associated outputs.

If changes are needed or errors detected during the course of use, the lead programmer changes the SAS program status from "in production" back to "in development" which then automatically prevents the SAS program's further use in the workflow until its status is again changed to "in production." As indicated in FIG. 5A, if a change is needed after the SAS program is changed back to "in production" it is returned to the control of the SAS programmer who makes changes and then makes it ready again for validation, as needed.

"Desktop application" should be taken to mean an application that runs stand-alone on a desktop or a laptop computer using an operating system like WINDOWS or LINUX, and not a web application, which requires a web browser to run.

As used herein a "processor" should be taken to include one or a plurality of processors used to perform a task, such as executing SAS program code, processing data for a GUI, or reading or writing from memory and includes a general purpose computer.

As used herein a "user" should be taken to include an actual person using an application locally, or accessing the application remotely using a web browser or a remote desktop program (RDP) using a computer located remotely. In the preferred embodiment the user runs the application as a desktop application, or accesses the desktop application remotely.

As used herein, a "computer" should be taken to include computers that have a hard disk drive for reading from and writing to a hard disk, a magnetic disk drive for reading from or writing to a removable magnetic disk, and an optical disk drive for reading from or writing to a removable optical disk such as a CD ROM, DVD, or other optical media. The hard disk drive, magnetic disk drive, and optical disk drive are connected to the system bus by a hard disk drive interface, a magnetic disk drive interface, and an optical drive interface, respectively. The drives and their associated computer-readable media provide nonvolatile (non-transitory) storage of computer readable instructions, data structures, programs, and other data for the computer system.

As used herein, a "database" should be taken to include a centralized or distributed database and includes a SQL database.

As used herein, the term "data" should be taken to include any information (excluding signals), contained in machine readable memory of a file system or used in a database or other structured data, or unstructured data representation in transitory or non-transitory memory.

As herein used, an "input device" should be taken to include a keyboard, mouse, pointer, touch pad, voice recognizer or other forms of input devices connected to a computer (with or without a display) for making modifications to, exploring, accessing, or generating electronic content that may be stored in memory.

As herein used, "display" is an LCD/LED type display or other types of display devices connected to the computer and capable of rendering and receiving input using a GUI or displaying other information generated by an application running on the computer executing machine executable code.

As used herein, the term "module" or "component" refers to a software or source code file, or set of software instructions contained, or not contained in a source code file and existing on a non-transitory or transitory memory medium. A module may exist as a stand-alone program or represent a program called by another program. A "component" is a portion of a "module" in the sense that the module calls a component to perform a task or task(s) portion of the module.

As used herein "memory" should be taken to include a machine-readable medium, either transient computer-readable storage medium or non-transient computer-readable storage medium. In various embodiments, the volatile (transient) portion of memory may be implemented using any suitable memory technology, such as static random access memory (SRAM), synchronous dynamic RAM or any other type of memory. While the examples of memory as shown and described may refer to a single machine-readable medium, memory should be taken to include a single medium or multiple media (e.g., a centralized or distributed database, and/or associated caches and servers, and or a variety of storage media, such as the processor registers, memories, and the storage device) that store one or more sets of machine-executable code or data. The term "machine-readable medium" shall also be taken to include any medium that is capable of storing, encoding or carrying a set of instructions for execution by the machine and that cause the machine to perform any one or more of the methodologies of the present invention, or that is capable of storing, encoding or carrying data structures utilized by or associated with such a set of instructions. The term memory shall accordingly be taken to include tangible media, such as solid-state memories and optical and magnetic media.

As used herein "module" should be taken to include a unit of distinct functionality that can provide information to, and receive information from, other modules. Accordingly, described modules may be regarded as being communicatively coupled. Modules may also initiate communication with input or output devices, and can operate on a resource (e.g., a collection of information, such as a database). Modules may include hardware circuitry, optical components, single or multi-processor circuits, memory circuits, software program modules and objects, firmware, and combinations thereof, as appropriate for particular implementations of various embodiments. The term "module" can include an identifiable portion of code, data, or a computational object to achieve a particular function, operation, processing, or procedure.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in claims should not be construed to limit the invention to the specific embodiments disclosed in the specification.

Additional aspects of invention are described in the following CONCEPTS 1-21.

CONCEPT 1. A system for managing a workflow for biomedical development, the system for managing the workflow comprising:
  a processor;
  one or more input devices;
  machine executable code, residing in non-transitory memory accessible to the processor, that when executed by the processor performs the following tasks in response to input received through the one or more input devices:
    create and make changes to workflow data used during the workflow, the workflow data comprising SAS programs used to produce biostatistical output from biomedical data, the workflow data being categorized and maintained under a life science program and a blind study or an un-blind study under the program, the blind or un-blind study producing the biomedical data, and further characterized under a milestone for the study;
    create and make changes to a SAS program data structure comprising one of the SAS programs and metadata associated with the SAS program, the metadata including:
      (a) a location for SAS source code, input files and output files,
      (b) a designated at least one programmer responsible for creating, updating and/or validating the source code during the course of the workflow, and
      (c) a status level indicating whether the source code is available for use, or not ready for use, by a biostatistician that will use the SAS program to produce the biostatistical output;
    create or add to an audit trail for the SAS program data structure during the course of the workflow, wherein if a change is made in the SAS program data structure, storing in memory an audit trail record containing information about the change, including
      (1) a user that made the change,
      (2) when the change was made, and
      (3) a type of change that was made.

CONCEPT 2. The system of CONCEPT 1, wherein the executing machine code further generates a m5 data structure compatible with a module 5 (m5) format of the eCTD, wherein the m5 data structure comprises a portion of the workflow data structure, the portion corresponding to the data files and source code used to reproduce the biostatistical output.

CONCEPT 3. The system of any one of CONCEPTS 1-2, wherein the workflow data is arranged in a folder logically arranged according to the life science program, the study, and the milestone, and under the milestone data maintained in at least the following folders are modified during the course of the workflow:
  (a) a programs folder comprising SAS programs,
  (b) the data used by each of the SAS programs to produce the biostatistical output, and
  (c) the documents used to communicate results from the biostatistical output.

CONCEPT 4. The system of any one of CONCEPTS 1-3, wherein the m5 data structure is generated by selecting each of the milestone folders (a), (b) and (c) using the input device, whereupon the respective data files contained therein are converted and formatted, as needed, and copied into memory in the m5 format for electronic submission to a regulatory agency.

CONCEPT 5. The system of any one of CONCEPTS 1-4, wherein a plurality of SAS program folders are under the programs folder and each of the SAS program folders contains one of the SAS program data structures.

CONCEPT 6. The system of any one of CONCEPTS 1-5, wherein the metadata for a SAS program further comprises a validation level designating a degree of validation required before the source code can be used by the biostatistician to produce the biostatistical output.

CONCEPT 7. The system of any one of CONCEPTS 1-6, wherein the machine executable code presents to the user a graphical user interface (GUI) for creating and making changes during the workflow, the GUI presenting a folder structure for accessing the data contained in folders using the input device.

CONCEPT 8. The system of any one of CONCEPTS 1-7, wherein the machine executable code further performs one or more of the following tasks in response to input received through the input device:
  making a SAS program available or unavailable for use when the programmer indicates the SAS program is ready for use and sending a message to the biostatistician that the SAS program is available or unavailable for use, respectively,
  provide access to the audit trail record to inspect changes made to the SAS program data, format and write a most recent or final version of data and source code from the data structure to the m5 folder at the completion of the workflow, and/or change user access rights to blinded study data.

CONCEPT 9. The system of any one of CONCEPTS 1-8, wherein the audit trail record and data structure are stored in a database and a module of the machine executable source code uses machine executable code associated with the database to determine when the change is made and to update the audit trail.

CONCEPT 10. A computer-implemented method for managing a workflow, the computer-implemented method comprising:
accessing in memory biomedical data relating to a milestone of a blinded or un-blinded study;
using a workflow space, conducting a workflow for performing a biostatistical analysis (BA) of the biomedical data using SAS programs, the workflow comprising:
  using a first SAS program, performing a biostatistical analysis on the biomedical data to produce a first output,
  creating a second SAS program during the course of the workflow and, using the second program to perform BA on the biomedical data to produce a second output,
  updating an audit trail during the course of the workflow,
  changing a status of the first program from in-production to in-development, changing access rights to the first program, modifying the first program, and after the modification changing its status from in-development to in-production, and
  at the conclusion of the workflow, copying a latest version of the first program and the second program to an m5 folder.

CONCEPT 11. An apparatus comprising machine executable instructions or code stored in non-transitory memory that when executed by one or more processors performs the following method in response to input received from an input device,
create and make changes to workflow data used during a workflow, the workflow data comprising SAS programs used to produce biostatistical output from biomedical data, the workflow data being categorized and maintained under a life science program and a blind study or an un-blind study under the program, the blind or un-blind study producing the biomedical data, and further characterized under a milestone for the study;
  create and make changes to a SAS program data structure comprising one of the SAS programs and metadata associated with the SAS program, the metadata including:
    (a) a location for SAS source code, input files and output files,
    (b) a designated at least one programmer responsible for creating, updating and/or validating the source code during the course of the workflow, and
    (c) a status level indicating whether the source code is available for use, or not ready for use, by a biostatistician that will use the SAS program to produce the biostatistical output;
  create or add to an audit trail for the SAS program data structure during the course of the workflow, wherein if a change is made in the SAS program data structure, storing in memory an audit trail record containing information about the change, including
    (1) a user that made the change,
    (2) when the change was made, and
    (3) a type of change that was made.

CONCEPT 12. The method of any one of CONCEPT 11, wherein the first program is validated by a validation program before being changed from in-development to in-production.

CONCEPT 13. The method of any one of CONCEPTS 11-12, wherein the m5 contains reformatted data and files, including
  the first program used to produce the first output,
  the second program used to produce the second output, and
  all data files needed to produce the first and second outputs.

CONCEPT 14. The method of any one of CONCEPTS 11-13, wherein the updating the audit trail comprises monitoring using database resources whether changes are made to either SAS program.

CONCEPT 15. The method of any one of CONCEPTS 11-14, wherein the audit trail table comprises a chronology of changes and nature of changes during the course of the workflow including at least a user name, date and time, and the record portion of a data structure that was changed.

CONCEPT 16. The method of any one of CONCEPTS 11-15, wherein the updating the audit trail includes updating an audit trail for any changes in a SAS TOC during the workflow.

CONCEPT 17. The method of any one of CONCEPTS 11-16, wherein the workflow is managed through a graphical user interface having a system of menus accessible to a plurality of users assigned to the workflow, the menus comprising a menu for accessing one or more of:
  the SAS program and metadata associated with the SAS program,
  the entire plurality of programs and data used, created and updated during the course of the workflow,
  access rights permission for selecting and de-selecting users having access rights to blinded clinical study data, and
    an audit trail record to inspect and identify when a change was made and by whom.

CONCEPT 18. An apparatus comprising machine executable instructions or code stored in non-transitory memory that when executed by one or more processors performs the machine executed portions of the system, or method of any one of CONCEPTS 1-17, respectively.

CONCEPT 19. A system for maintaining a SAS source file used to perform a biostatistical analysis of biomedical data during the course of a workflow, the system comprising:
  a processor and input device;
  machine executable code, residing in non-transitory memory accessible to the processor, that when executed by the processor performs the following tasks in response to user input received through a graphical user interface generated by the machine executable code and displayable to the user through the user interface:
    create and make changes to a workflow data structure used during the workflow, the data structure comprising metadata associated with a SAS program intended for being used to produce biostatistical output from biomedical data, comprising
      a SAS programmer, validating programmer and lead programmer responsible for creating the SAS program,
      a validation level for the SAS program indicating the level of validation needed before the program may be used by a biostatistician to produce the biostatical output, and
      a program status as one of planned, in-development, ready for validation and in-production;

wherein a method for creating or editing the SAS program includes the following steps in the following order, (a) send a first message to the SAS programmer to create or make changes to source code, and set program status to in-production, (b) send a second message to one or both of the validating or lead programmer, indicating that source code is ready for review or validation, and change status to ready for validation, (c) send a third message to the biostatistician indicating that the SAS program is ready for use by the biostatistician, and change program status to in-production, and (d) if change is needed to the source code, repeat steps (a) through (c), thereby restricting access to the SAS program to only the SAS programmer, validating programmer and lead programmer.

CONCEPT 20. The system of any one of CONCEPTS 1-19, wherein the validation level comprises three validation levels, wherein a level 1 validation is self-review by the programmer and log check a level 2 validation is spot check and code review by a reviewing programmer, and a level 3 validation is a second programmer independently creates source code to check for same output.

CONCEPT 21. The system of method of any one of CONCEPTS 1-20, further comprising a desktop application comprising the machine executable code, or a web based application comprising the machine executable code.

What is claimed is:

1. A system for managing a workflow for biomedical development, the system for managing the workflow comprising:

a processor;

one or more input devices;

a desktop application having machine executable code, residing in non-transitory memory accessible to the processor, that when executed by the processor performs the following tasks in response to input received through the one or more input devices:

create and make changes to workflow data used during the workflow, the workflow data comprising SAS programs used to produce biostatistical output from biomedical data, the workflow data being categorized and maintained under a life science program and a blind study or an un-blind study under the program, the blind or un-blind study producing the biomedical data, and further characterized under a milestone for the study;

create and make changes to a SAS program data structure comprising one of the SAS programs and metadata associated with the SAS program, the metadata including:

(a) a location for SAS source code, input files and output files, (b) a designated at least one programmer responsible for creating, updating and/or validating the source code during the course of the workflow, and (c) a status indicating whether the source code is available for use, or not ready for use;

create or add to an audit trail for the SAS program data structure during the course of the workflow, wherein if a change is made in the SAS program data structure, storing in memory an audit trail record containing information about the change, including (1) a user that made the change, (2) when the change was made, and (3) a type of change that was made.

2. The system of claim 1, wherein the executing machine code further generates a m5 data structure compatible with a module 5 (m5) format of the eCTD, wherein the m5 data structure comprises a portion of the workflow data structure, the portion corresponding to the data files and source code used to reproduce the biostatistical output.

3. The system of claim 2, wherein the workflow data is arranged in a folder logically arranged according to the life science program, the study, and the milestone, and under the milestone data maintained in at least the following folders are modified during the course of the workflow:

(a) a programs folder comprising SAS programs, (b) the data used by each of the SAS programs to produce the biostatistical output, and (c) the documents used to communicate results from the biostatistical output.

4. The system of claim 3, wherein the m5 data structure is generated by selecting each of the milestone folders (a), (b) and (c) using the input device, whereupon the respective data files contained therein are converted and formatted, as needed, and copied into memory in the m5 format for electronic submission to a regulatory agency.

5. The system of claim 3, wherein a plurality of SAS program folders are under the programs folder and each of the SAS program folders contains one of the SAS program data structures.

6. The system of claim 1, wherein the metadata for a SAS program further comprises a validation level designating a degree of validation required before the source code can be used by the biostatistician to produce the biostatistical output.

7. The system of claim 1, wherein the machine executable code presents to the user a graphical user interface (GUI) for creating and making changes during the workflow, the GUI presenting a folder structure for accessing the data contained in folders using the input device.

8. The system of claim 1, wherein the machine executable code further performs one or more of the following tasks in response to input received through the input device:

making a SAS program available or unavailable for use when the programmer indicates the SAS program is ready for use and sending a message to the biostatistician that the SAS program is available or unavailable for use, respectively, provide access to the audit trail record to inspect changes made to the SAS program data, format and write a most recent or final version of data and source code from the data structure to the m5 folder at the completion of the workflow, and/or change user access rights to blinded study data.

9. The system of claim 1, wherein the audit trail record and data structure are stored in a database and a module of the machine executable source code uses machine executable code associated with the database to determine when the change is made and to update the audit trail.

10. An apparatus comprising machine executable instructions or code stored in non-transitory memory that when executed by one or more processors performs the following method in response to input received from an input device, create and make changes to workflow data used during a workflow, the workflow data comprising SAS programs used to produce biostatistical output from biomedical data, the workflow data being categorized and maintained under a life science program and a blind study or an un-blind study under the program, the blind or un-blind study producing the biomedical data, and further characterized under a milestone for the study;

create and make changes to a SAS program data structure comprising one of the SAS programs and metadata associated with the SAS program, the metadata including:
(a) a location for SAS source code, input files and output files,
(b) a designated at least one programmer responsible for creating, updating and/or validating the source code during the course of the workflow, and
(c) a status level indicating whether the source code is available for use, or not ready for use, by a biostatistician that will use the SAS program to produce the biostatistical output;

create or add to an audit trail for the SAS program data structure during the course of the workflow, wherein if a change is made in the SAS program data structure, storing in memory an audit trail record containing information about the change, including
(1) a user that made the change,
(2) when the change was made, and
(3) a type of change that was made.

11. The method of claim 10, wherein the first program is validated by a validation program before being changed from in-development to in-production.

12. The method of claim 10, wherein the m5 contains reformatted data and files, including
the first program used to produce the first output,
the second program used to produce the second output, and
all data files needed to produce the first and second outputs.

13. The method of claim 10, wherein the updating the audit trail comprises monitoring using database resources whether changes are made to either SAS program.

14. The method of claim 10, wherein the audit trail table comprises a chronology of changes and nature of changes during the course of the workflow including at least a user name, date and time, and the record portion of a data structure that was changed.

15. The method of claim 10, wherein the updating the audit trail includes updating an audit trail for any changes in a SAS TOC during the workflow.

16. The method of claim 10, wherein the workflow is managed through a graphical user interface having a system of menus accessible to a plurality of users assigned to the workflow, the menus comprising a menu for accessing one or more of:
the SAS program and metadata associated with the SAS program,
the entire plurality of programs and data used, created and updated during the course of the workflow,
access rights permission for selecting and de-selecting users having access rights to blinded clinical study data, and
an audit trail record to inspect and identify when a change was made and by whom.

17. An apparatus comprising machine executable instructions or code stored in non-transitory memory that when executed by one or more processors performs the method of claim 1.

18. A system for maintaining a SAS source file used to perform a biostatistical analysis of biomedical data during the course of a workflow, the system comprising:
a processor and input device;
machine executable code, residing in non-transitory memory accessible to the processor, that when executed by the processor performs the following tasks in response to user input received through a graphical user interface generated by the machine executable code and displayable to the user through the user interface:
create and make changes to a workflow data structure used during the workflow, the data structure comprising
metadata associated with a SAS program intended for being used to produce biostatistical output from biomedical data, comprising
a SAS programmer, validating programmer and lead programmer responsible for creating the SAS program,
a validation level for the SAS program indicating the level of validation needed before the program may be used by a biostatistician to produce the biostatical output, and
a program status as one of planned, in-development, ready for validation and in-production;
wherein a method for creating or editing the SAS program includes the following steps in the following order,
(a) send a first message to the SAS programmer to create or make changes to source code, and set program status to in-production,
(b) send a second message to one or both of the validating or lead programmer, indicating that source code is ready for review or validation, and change status to ready for validation,
(c) send a third message to the biostatistician indicating that the SAS program is ready for use by the biostatistician, and change program status to in-production, and
(d) if change is needed to the source code, repeat steps (a) through (c), thereby restricting access to the SAS program to only the SAS programmer, validating programmer and lead programmer.

19. The system of claim 18, wherein the validation level comprises three validation levels, wherein
a level 1 validation is self-review by the programmer and log check
a level 2 validation is spot check and code review by a reviewing programmer, and
a level 3 validation is a second programmer independently creates source code to check for same output.

* * * * *